(12) United States Patent
Featonby et al.

(10) Patent No.: US 10,458,834 B2
(45) Date of Patent: Oct. 29, 2019

(54) RADIATION DETECTOR (71) Applicant: JOHNSON MATTHEY PUBLIC LIMITED COMPANY, London (GB)

(72) Inventors: Paul David Featonby, Northumberland (GB); Timothy Hough, Durham (GB); Geoffrey Stuart Howe, Durham (GB)

(73) Assignee: Johnson Matthey Public Limited Company, London, England (GB)

( * ) Notice: Subject to any disclaimer, the term of this patent is extended or adjusted under 35 U.S.C. 154(b) by 572 days.

(21) Appl. No.: 14/423,863

(22) PCT Filed: Sep. 5, 2013

(86) PCT No.: PCT/GB2013/052331
§ 371 (c)(1),
(2) Date: Feb. 25, 2015

(87) PCT Pub. No.: WO2014/076448
PCT Pub. Date: May 22, 2014

(65) Prior Publication Data
US 2015/0241262 A1 Aug. 27, 2015

(30) Foreign Application Priority Data

Sep. 6, 2012 (GB) .................... 1215919.0

(51) Int. Cl.
*G01T 1/185* (2006.01)
*G01F 23/288* (2006.01)
(Continued)

(52) U.S. Cl.
CPC ........ *G01F 23/288* (2013.01); *G01F 23/2885* (2013.01); *G01N 9/24* (2013.01);
(Continued)

(58) Field of Classification Search
CPC ..... G01F 23/2885; G01F 23/288; G01T 7/00; G01T 1/185; G01T 1/20; G01N 9/24; H01J 47/08
(Continued)

(56) References Cited

U.S. PATENT DOCUMENTS 3,668,392 A  6/1972 Bajek et al.
4,245,479 A  1/1981 Richter, Jr. et al.
(Continued)

FOREIGN PATENT DOCUMENTS

CN  2013/68919 Y  12/2009
DE  199 26 388 A1  12/2000
(Continued)

OTHER PUBLICATIONS

International Search Report, dated Jun. 5, 2014, from corresponding PCT application.
(Continued)

*Primary Examiner* — David P Porta
*Assistant Examiner* — Gisselle Gutierrez
(74) *Attorney, Agent, or Firm* — BakerHostetler (57) ABSTRACT

A detector probe, for detecting ionizing radiation and which is suitable for use in a nucleonic instrument usable in locations having a high ambient temperature, includes an array of radiation detectors mounted on a support and a heat pipe for cooling the detector probe. The nucleonic instrument incorporating such a detector probe is also described.

12 Claims, 3 Drawing Sheets (51) Int. Cl.
  *G01T 7/00*   (2006.01)
  *G01N 9/24*   (2006.01)
  *G01T 1/20*   (2006.01)
  *H01J 47/08*  (2006.01)

(52) U.S. Cl.
  CPC ............ *G01T 1/185* (2013.01); *G01T 1/20* (2013.01); *G01T 7/00* (2013.01); *H01J 47/08* (2013.01)

(58) Field of Classification Search
  USPC ..................................................... 250/357.1
  See application file for complete search history.

(56) References Cited

U.S. PATENT DOCUMENTS

| | | | |
|---|---|---|---|
| 4,733,082 A | 3/1988 | Moore et al. | |
| 4,893,016 A | 1/1990 | Katagiri | |
| 5,111,874 A * | 5/1992 | Kosson | F25D 19/006 |
| | | | 165/104.26 |
| 6,236,051 B1 | 5/2001 | Yamakawa et al. | |
| 6,359,281 B1 * | 3/2002 | Pawlak | G01T 1/243 |
| | | | 250/370.09 |
| 6,380,544 B1 | 4/2002 | Broerman | |
| 2005/0067579 A1 | 5/2005 | Tsuchiya et al. | |
| 2005/0285046 A1 | 12/2005 | Iwanczyk et al. | |
| 2008/0011950 A1 | 1/2008 | Rose et al. | |
| 2010/0090121 A1 | 4/2010 | Burks et al. | |
| 2011/0044427 A1 * | 2/2011 | Featonby | G01F 23/288 |
| | | | 378/52 |
| 2014/0175290 A1 * | 6/2014 | Field | G01N 9/24 |
| | | | 250/361 R |

FOREIGN PATENT DOCUMENTS

| | | | | |
|---|---|---|---|---|
| EP | 0 060 630 A2 | | 9/1982 | |
| GB | 717753 A | | 3/1952 | |
| GB | 2219396 A | | 12/1989 | |
| GB | 2493844 A | * | 2/2013 | ........... G01F 23/288 |
| JP | 58202883 A | | 11/1983 | |
| JP | H03 165223 A | | 7/1991 | |
| JP | H06265640 A | | 9/1994 | |
| WO | 87/05990 A1 | | 10/1987 | |
| WO | 00/22387 A1 | | 4/2000 | |
| WO | 01/23851 A1 | | 4/2001 | |
| WO | 2004/077096 A2 | | 9/2004 | |
| WO | 2007/086591 A1 | | 8/2007 | |
| WO | 20100032064 | | 3/2010 | |

OTHER PUBLICATIONS

GB Search Report, dated Feb. 11, 2014, from corresponding GB application.
GB Search Report, dated Dec. 21, 2012, from corresponding GB application.

* cited by examiner

RADIATION DETECTOR

BACKGROUND OF THE INVENTION

Field of the Invention

The present invention relates to an apparatus for measuring levels of materials, especially of fluids, and optionally for calculating a density profile of a mixed fluid system.

Description of the Related Art

A density profiler has been described in WO2000/022387. The device comprises a linear array of sources of ionising radiation which emit radiation towards detectors disposed in one or more linear arrays. When the source array and detector array(s) are positioned so that they traverse the interfaces between two or more fluids in a container, the interfaces of the fluids may be identified from the differences in radiation received by each detector in the array. The device has been successfully deployed for use in storage tanks and oil separators. In some circumstances it is required to operate density profilers in hot locations or where there is a risk that the instrument will be subjected to very high temperatures at certain times. Many electronic instruments are sensitive to operation in extreme temperatures and cannot be certified for use above a particular temperature. Of particular relevance to the field of nucleonic instruments, it is known that the lifetime of components such as Geiger-Müller tubes may be shortened by operation at high temperature. It is therefore an object of the invention to provide a nucleonic instrument such as a density profiler or other nucleonic level measurement system which may be operated in high environmental temperatures and which overcomes some of the known problems.

According to the invention, we provide a detector probe, said detector probe comprising at least one radiation detector for detecting ionising radiation comprising alpha particles, beta particles, gamma radiation and/or neutrons, said detector being mounted on a support and characterised in that said detector probe is provided with at least one heat pipe for cooling the detector probe.

According to the invention, we further provide a nucleonic instrument for measuring a characteristic of one or more material phases within a container, comprising a source of ionising radiation comprising alpha particles, beta particles, gamma radiation and/or neutrons, at least one detector probe according to the invention, a power source, and electronic apparatus comprising a control unit and a signal and data processing means for calculating a characteristic of the material phases using signals generated by the detectors in response to radiation received from the radiation sources.

A density profiler according to the invention comprises:
(a) an array of sources of ionising radiation comprising alpha particles, beta particles, gamma radiation and/or neutrons,
(b) at least one detector probe for detecting ionising radiation comprising an array of radiation detectors mounted on a support,
(c) a power source, and electronic apparatus comprising a control unit and a signal and data processing means for calculating a characteristic of the material phases using signals generated by the detectors in response to radiation received from the radiation sources; the power source and electronic apparatus being housed within an enclosure supported mounted adjacent to the detector probe,
characterised in that said detector probe is provided with at least one heat pipe for cooling the detector probe.

The detector probe is cooled by means of at least one heat pipe. Heat pipes typically comprise a thermally conductive, usually metal, sealed tube, containing a small volume of a liquid, the space within the tube being at a reduced pressure compared with atmospheric pressure. The tube may also contain a means, such as a wick material, for assisting the evaporation and condensation of the liquid within the tube. In use, a heat pipe can transport heat from a first, lower end to its second, upper end by evaporation of the liquid at the lowest part of the tube and condensation of the liquid vapour at a higher, cooler part of the tube. Whilst the use of a "lower" and "upper" part of the heat pipe is used to explain the general mode of operation of a heat pipe, it is noted that a heat pipe may also be used in a horizontal position or any other position between vertical and horizontal and that this invention is not limited to the placement of the heat pipe in a vertical plane.

The use of a heat pipe for cooling the detector probe has a number of advantages. Heat pipes are simple compact cooling devices, having no moving parts such as pumps for circulating coolant fluids, and requiring no power to operate. They therefore require no maintenance after installation. The provision of a powered cooling device to the detector probe of the invention would require additional electrical connections to be made which may complicate the design of the probe as an intrinsically safe electrical apparatus.

The heat pipe is normally an elongate structure. The cross-section may be any suitable shape. Although many heat pipes have a circular cross-section, other shapes are also suitable, including square, elliptical or irregular. An irregular shape may be used, for example, to better fit the heat pipe into the detector probe, and/or around or between other components of the detector probe. Various types of heat pipe are available containing different coolant fluids which are suitable for different applications. Their use in cooling nucleonic instruments used in hot environments has not been previously described. The heat pipe used to cool the detector probe is typically made from copper and contains a liquid and a wicking material extending at least a part of the distance between first and second ends of the heat pipe. The liquid may be an aqueous liquid or a non-aqueous liquid. In some embodiments of the invention it is advantageous to use a heat pipe containing a liquid which has a low freezing temperature, particularly a liquid having a freezing temperature that is less than 0° C., especially less than −10° C., particularly less than −20° C. The use of a liquid having a low freezing point reduces the risk of the coolant liquid freezing when a portion of the heat pipe is exposed to cold environments. Typical wicking materials include foams (e.g. metal foams), sintered materials, woven or non-woven fibrous materials, meshes, or a channel in the heat pipe wall. More than one heat pipe may be employed in the instrument. When more than one heat pipe is used, they may be of similar size and construction or different. Two or more heat pipes, if present, may be thermally coupled together or they may each be independent of other cooling means in the instrument.

The heat pipe(s) extend between the detector probe, or a part thereof, and a cooler location, which is normally outside the detector probe and may be external to the instrument, which experiences lower ambient temperatures. The heat pipe(s) normally operate to transfer heat from within the detector probe to a location external to the instrument. The heat pipe may be straight or it may be include angular or curved portions. A flexible or jointed heat pipe may be used. When two or more heat pipes are used, they may be joined together using a suitable thermally conductive coupling. The coupling may join two or more heat pipes so that their longitudinal axes are parallel or angled. The heat pipes may be designed such that two heat pipes may be joined in such a way that they contact each other at an interfacial surface. A portion of a heat pipe which is intended to interface with another heat pipe may have a surface which is complementary to a surface on the other heat pipe. For example, heat pipes may be provided which each have a flattened interfacial portion so that two such pipes can be connected together with their flattened portions in contact with each other. Interfacial surfaces for connecting together heat pipes need not, however, be flat. They may also carry means such as interlocking members which facilitate the connection between two or more heat pipes. Heat pipes may be connected together using a coupling which is jointed to allow the heat pipes to be moved. Such a coupling may include a hinge for rotational movement around a hinge point or a more complex joint such as a ball joint if movement in more than one plane is required. Coupled heat pipes, especially with a jointed coupling, may be useful for assembling and/or installing long detector probes when space is limited.

A portion of the heat pipe outside the detector probe may dissipate heat to its surrounding environment. This function can be assisted if a heat sink, optionally but preferably including heat dissipating means, such as fins, is thermally coupled to that portion of the heat pipe which is intended to dissipate heat. A heat sink may be formed from any suitable material; copper and aluminium are examples of suitable materials. A separate heat sink may be provided for each heat pipe present in the detector probe, or alternatively more than one heat pipe may be connected to the same heat sink. The heat sink may be detachable from the heat pipe; such an arrangement may be useful when assembling or disassembling a detector probe in an area having a restricted amount of space.

In one embodiment the heat pipe is angled, so that the portion of the heat pipe extending outside the detector probe does not carry heat to a housing containing electronic apparatus, which typically in that embodiment, is positioned above the detector probe. In an alternative embodiment, a heat sink is provided above the detector probe and in thermal contact with the heat pipe. A heat sink, particularly if provided with heat dissipating fins, may be protected by a cover or similar protective shroud. Such a cover or shroud is preferably designed to allow the circulation of air around the heat sink. This can be achieved using a cover or shroud formed from a perforate material such as a mesh or expanded metal.

The external portion of the heat pipe, including any heat dissipating means provided, may be protected from environmental damage by means of a coating or treatment, such as plating, e.g. with nickel or a nickel alloy. The external portion of the heat pipe, including any heat dissipating means provided, may be supported by means of a support framework. When the external environment is very cold, e.g. at a temperature <−10° C., the heat dissipating means may develop a coating of ice if allowed to cool, such as when the temperature within the detector probe is not sufficient to require cooling. It may therefore be necessary to provide heat, e.g. by means of electrically operated trace heating to the heat dissipating means to ensure their reliable operation. The use of a heat pipe containing a coolant liquid which has a low freezing point, should be considered when the heat dissipating means may be exposed to such cold environments. Preferably the coolant liquid selected for such use has a freezing point which is at a lower temperature than the lowest environmental temperature for which the detector probe is specified.

SUMMARY OF THE INVENTION

The detector probe comprising the detectors, electrical components, such as circuit boards, and heat pipe(s), is preferably surrounded by a protective layer, such as a plastic tube. The detector probe comprising the detectors, electrical components and heat pipe(s), all optionally surrounded by a protective layer, is preferably housed within a protective housing, preferably formed from a tough and rigid material. The housing is made from a material which is sufficiently transparent to the radiation to be detected by the detectors for the detector probe to perform its function. A suitable material for the housing is titanium which can be formed to be sufficiently strong at a thickness which remains substantially transparent to gamma radiation. In use the detector probe may be placed within a dip tube or dip pipe. The detector probe may further comprise a thermally insulating material arranged between the detectors and the electronic components of the probe and an external housing of the detector probe in order to help maintain the temperature of the detectors within a desired range of temperatures. Normally the insulation is provided in as thin a layer as possible, in order to reduce the dimensions of the probe. For this reason, insulating materials having a very low thermal conductivity are preferred. A preferred form of detector probe, suitable for use in a density profiler, comprises an electrical circuit board, a plurality of radiation detectors and a heat pipe and optionally an elongate support, all enclosed within a rigid housing, and thermal insulation between the inner wall of the housing and the detectors.

The skilled person will appreciate that the selection of a suitable insulating material is dependent upon the characteristics required. In one embodiment, we have found that a suitable thermal insulator has a thermal conductivity ($\kappa$)<0.05 W/m/K, and especially <0.005 W/m/K. The insulation may or may not include evacuated compartments. We have, however, found that the materials used to form such panels may not be capable of maintaining a vacuum at high temperatures. The insulation may include metallised portions.

The detector probe comprises a support and at least one radiation detector mounted on the support. By support, we mean any object or structure which can support the detector in the desired position for detecting radiation in use. When the detector requires electrical power, such as a Geiger Müller tube or a photomultiplier tube attached to a scintillation detector, a powered circuit is present to deliver power to the detector(s), to enable control signals to pass to the detector from a control unit and to carry data signals from the detector to a signal processor and data processor. In one preferred form, each detector is mounted on a printed circuit board for carrying the control and data signals to and from the detector. A printed circuit board may serve as a support for the detector(s). In this form, the circuit board may be provided with a reinforcing structure, such as a stiffening rod or plate in order to provide strength and stiffness over the length of the probe. The heat pipe may function to support and provide rigidity to the detectors and their associated electrical apparatus.

When space within the detector probe is limited, it may be preferred to provide more than one circuit board, each being mounted in a different location. This arrangement enables the function of a relatively wide circuit board to be split between two or more smaller boards which can be arranged to require a smaller space within the detector probe. As an example a detector may be located between two circuit boards. One such board may be configured to handle control and measurement signals to and from the detector, whilst the other is configured to provide electrical power to the detector.

When a detector probe is intended for use in a hazardous location, where potentially explosive gas mixtures may be present continuously or intermittently at some time during operation of the probe, the probe and the heat source are designed to be intrinsically safe, as defined by the appropriate standards including the current version of European Standard EN 60079:2009, especially parts 0, 10 and 11 thereof. Intrinsically safe has the meaning given in the standards. Intrinsically safe is a widely used term having a precise meaning that is understood by the skilled person. According to European Standard EN 60079:2009 and British Standard BS EN 60079-11:2012, intrinsic safety is a type of protection based on the restriction of electrical energy within equipment and of interconnecting wiring exposed to the explosive atmosphere to a level below that which can cause ignition by either sparking or heating effects.

An intrinsically safe circuit is a circuit in which any spark or any thermal effect produced in the conditions specified in the standard, which include normal operation and specified fault conditions, is not capable of causing ignition of a given explosive atmosphere. An intrinsically safe electrical device is a device in which all of the electrical circuits are intrinsically safe circuits. The design and selection of components and the test criteria applied to such equipment is governed by national and international standards such as BS EN 60079-11:2012 and its related parts, including part 0 concerning general requirements for electrical equipment intended for use in explosive atmospheres. Preferably the detector probe conforms at least to Level of Protection ib of the standard, i.e. it is designed to be safe in use in explosive atmospheres in normal operation and with the application of those non-countable faults which give the most onerous condition; and in normal operation and with the application of one countable fault plus the application of those non-countable faults which give the most onerous condition as defined in section 5.3 of BS EN 60079-11:2012. Countable faults and non-countable faults are defined in BS EN 60079-11:2012 at paragraph 3.7. Most preferably, the detector probe conforms to Level of Protection is of the standard, i.e. it is designed to be safe in use in explosive atmospheres when the circuit contains two countable faults as defined in section 5.2 of BS EN 60079-11:2012. Such protection is achieved by the use of various components and construction methods which include, for example, the separation of parts of the circuits by minimum separation distances as set out in section 6.3 "Separation Distances" of BS EN 60079-11:2012.

The heat pipe may operate to remove heat from the space surrounding the detectors and this arrangement may be adequate in some versions of the invention. In a preferred embodiment of the invention, the detectors are mounted in direct thermal contact with the heat pipe. In this embodiment, the detectors may be physically supported on the heat pipe, for example using means such as adhesive, a strap, clip, cable-tie or other connector. When the detectors are mounted in thermal contact with the heat pipe, heat can be removed from the detectors most efficiently. In this embodiment, the detectors are preferably electrically isolated from the heat pipe by means of a material which is both thermally conductive and electrically insulating. Such materials include grease, mica and composite materials such as the commercially available Sil-Pad™ range of materials supplied by the Bergquist company.

The detector probe comprises at least one detector for detecting ionising radiation emitted by a radiation source. The type of detector used may be selected by the person skilled in nucleonic instrument engineering, having regard to the properties of the radiation to be detected, the conditions in which the detector is to be used and the characteristics of radiation which are to be measured. Typically the detectors used are gaseous ionisation detectors, such as Geiger Müller tubes, or scintillation devices including scintillation crystals and organic scintillators with an associated photodetector such as a photomultiplier or photodiode. The detector probe may include one or more than one detectors, depending on the intended use of the detector probe.

When the detector probe is for use in a level gauge or density profiler, it typically has at least 4, preferably at least 10 detectors. A detector probe for use in a density profiler instrument for use in large vessels may include at least 20 detectors, more preferably at least 40 detectors, for example at least one hundred detectors in the longer probes. The detectors are preferably spaced apart and preferably arranged as a linear array of detectors. The size of the detectors affects the precision of level detection when the probe is used in a level gauge or density profiler. Therefore the size of detector(s), and their spacing, if more than one detector is used, is selected according to the demands of the use for which the detector probe is designed. When the detector probe is used to find a level (including in a density profile) with high precision then small detectors set in close proximity to each other are preferred. Suitable small Geiger Müller tubes have a diameter of from 10 mm to 25 mm, more preferably <20 mm. These detectors may have a length of from about 25 mm to >200 mm. Precision of a level gauge or density profiler can be increased by including overlapping detectors, which may be present in separate detector probes.

The nucleonic instrument according to the invention comprises a source of ionising radiation comprising alpha particles, beta particles, gamma radiation and/or neutrons, at least one detector probe according to the invention, a power source, and electronic apparatus comprising a control unit and a signal and data processing means for calculating a characteristic of the material phases using signals generated by the detectors in response to radiation received from the radiation sources. The nucleonic instrument preferably comprises a density profiler or a level gauge.

The electronic apparatus of the nucleonic instrument, comprising the control system, signal and data processing device, power source and optionally equipment such as data loggers and transmitting equipment, is normally housed within an enclosure in order to protect it from the environment. The enclosure is designed to withstand the conditions in which nucleonic instrument may be deployed, including those of super-ambient temperature and pressure. The temperature of the electronic apparatus within the enclosure is desirably maintained within a temperature range in which it can operate according to its designed function. Preferably the electronic apparatus is maintained at a temperature less than 120° C., more preferably less than 100° C. A temperature sensor may be provided to monitor the temperature at one or more locations within the enclosure. The enclosure may be supported mounted adjacent to the detector probe and source array or may alternatively be mounted in a position which is spaced apart from the detector probe. In the latter case, communication means, which may be wireless or wired, are provided to carry electrical signals between the detector probe and the electronic apparatus. The detector probe tends to conduct heat to or away from any associated electrical control system or data processing apparatus. When the detector probe is subjected to very high temperatures a corresponding increase in the temperature of associated apparatus may be reduced by means of thermal insulation placed between the detector probe and the associated apparatus. The enclosure may contain insulation material in order to thermally insulate the electronic apparatus from heat conducted by the detector probe and/or a source array, and/or to insulate the electronic apparatus from hot or cold external temperatures. In a preferred embodiment, the instrument comprises thermal insulation between the detector probe on the one hand and the power source and electronic apparatus on the other hand. In this way the electronic control, signal/data processing components and power source may be protected from high temperatures which might adversely affect their operation. In some environments, the detector probe may be subjected to high temperatures within a storage or process vessel, so as to require cooling, whilst the external environment is very cold, e.g. at a temperature <−10° C. It may therefore be necessary to provide heat to the enclosure and this may be achieved by means of electrically operated trace heating within the housing. Additional modifications may be made to adapt the nucleonic instrument for use in high temperature environments.

The level gauge of the invention comprises at least one source of ionising radiation and a detector probe as hereinbefore described, said source and detector probe being arranged so that ionising radiation from the source passes along a straight line through a portion of the container to the detector probe. The source is mounted within a radiation-shielding material which includes collimation means for producing a collimated beam of radiation which is directed towards the detector probe. The source and/or detector probe may be mounted outside or inside a vessel containing the material to be measured. When the source is mounted outside the vessel and the radiation is to traverse at least one vessel wall, the source must be selected to produce radiation of sufficient energy to penetrate the walls of the vessel. The source should also be selected to be of sufficient activity to produce sufficient counts in the detector(s) in order that a reproducible signal may be generated by the detectors which is proportional to the radiation detected within about a second so that level measurement may be carried out reasonably quickly. One or more than one sources may be used. Normally the number of sources used in a level gauge is not more than 10 and is preferably from 1-4. Each source may emit a beam of radiation towards more than one detector.

The density profiler according to the invention, for measuring a level of two or more material phases within a container, comprises a linear array of sources of radiation, at least one detector probe according to the invention for detecting ionising radiation, each comprising a linear array of radiation detectors mounted on a support, and a signal and data processing means for calculating a density profile of the material phases using signals generated by the detectors in response to radiation received from the sources; said source array and detector probe being arranged so that ionising radiation from each source passes along a straight line through a portion of the container to a detector carried on the detector probe. It has been found to be advantageous to provide more than one detector probe in a density profiler. Each source is collimated to provide at least one beam of radiation, each beam being directed to one detector located on a detector probe. The relative attenuation of the beams of radiation detected by different detectors, which are located at different positions in the material phases, may be used to calculate a density profile of the material phases. The source array of the density profiler according to the invention includes a plurality of radiation sources, which are preferably sources of gamma radiation. Normally the number of sources used in a density profiler is at least 4 and usually more than 10. Each source may emit a beam of radiation towards more than one detector.

The radiation emitted by the radiation source(s) comprises ionising radiation including alpha particles, beta particles, gamma radiation and neutrons. Preferably the ionising radiation detected by the detectors does not include X-rays. The source of ionising radiation is preferably not a source of X-rays. The radiation used is selected by the transparency to the radiation of the vessel and/or its contents (i.e. the attenuation coefficient of the medium) and the availability of suitable sources and detectors. Gamma radiation is preferred because it is useful for penetrating large solid structures such as process vessels. Suitable sources of gamma include $^{60}$Co and $^{137}$Cs, $^{133}$Ba, $^{241}$Am, $^{24}$Na and $^{182}$Ta, however any gamma-emitting isotope of sufficient penetrating power could be used, and many such are already routinely used in level measurement devices. For a permanent installation, a radioisotope source should be chosen to have a relatively long half-life to give the equipment a satisfactory service life. Usually, the half-life of the radioisotope used will be at least 2, and desirably at least 10, years. The half-lives of the radioisotopes mentioned above are: $^{137}$Cs gamma ca. 30 years, $^{133}$Ba ca. 10 years and $^{241}$Am ca. 430 years. Suitable sources generally emit radiation at energies between about 40 and 1500 keV and suitable detectors can detect such radiation with sufficient sensitivity that the radiation detected varies according to the density of the transmission medium. Desirably the source intensity will be at least about $4\times10^7$ more usually from $4\times10^8$ to $4\times10^9$, Becquerel (Bq). The use of sources with lower intensity may require unduly long integration times to obtain adequately precise results (signal to noise ratio) and more intense sources are relatively expensive and/or may lead to swamping of the detectors. $^{241}$Am and $^{137}$Cs sources having an intensity of about $1.7\times10^9$ Bq are readily commercially available and are suitable for use in this invention.

The energy of the source radiation used in a density profiler is typically not more than about 1400 keV and is desirably lower than this. Preferably the energy of the source radiation is not less than about 30 keV. The source can be a radioactive isotope as described above in connection with the level gauge. When the instrument is intended to be fitted into a vessel such as an oil separator through a standard port, the beam length is preferably less than 50 cm, more preferably less than 30 cm and for this use a less energetic source is desirable. Suitable low-energy sources include in particular $^{241}$Am which is a 60 keV gamma source. When using a higher energy source such as $^{137}$Cs in a density profiler, a greater path length is optimal, typically between 20 cm and 40 cm, e.g. about 30 cm. Other radioisotope sources can be used if desired. The use of low-energy sources makes equipment handling and source shielding safer and/or easier.

The source shielding and collimation means is shaped so that the emission of radiation is confined, so far as possible, to a beam of suitable width directed through the material which is to be measured towards one or more detectors.

Normally this is achieved by providing a channel or aperture through the shielding material surrounding the source, such that emission of radiation from the source is substantially confined to emission of a beam of radiation through the channel. It is often desirable to collimate the source radiation into more than one beam, e.g. by providing more than one channel in the shielding material, so that radiation from a single source may be directed at more than one detector. In this case, the detectors may be in different positions within or outside the vessel and they may form part of the same linear array or they may be located in different detector arrays.

BRIEF DESCRIPTION OF THE DRAWING FIGURES

The invention is further described, by way of example only, with reference to the accompanying drawings, which are.

Figure 1:
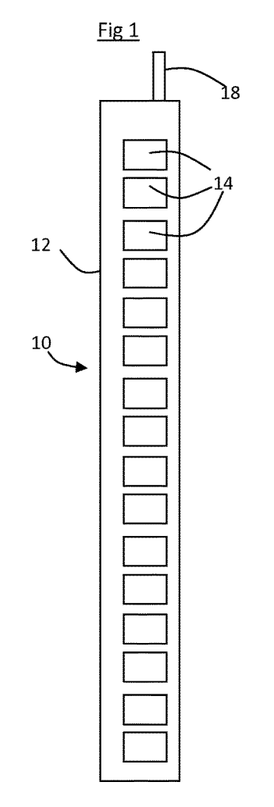
FIG. 1: A schematic diagram of a detector probe according to the invention.
Figure 1A:
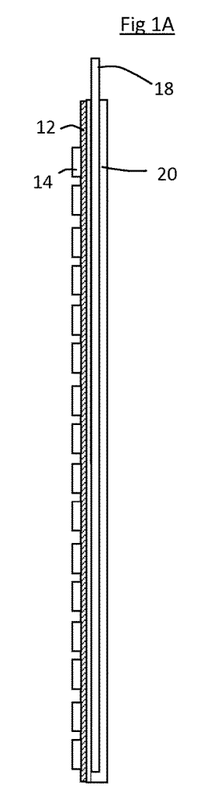
FIG. 1A: A schematic diagram of a side view of the detector probe in FIG. 1.
Figure 2:
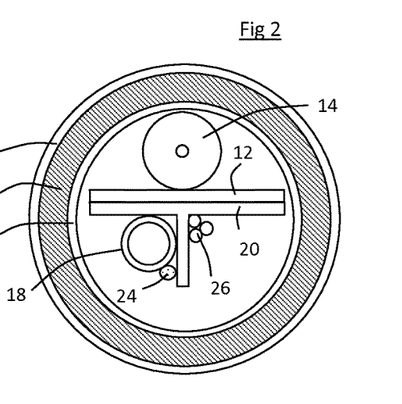
FIG. 2: A schematic diagram of transverse section through a detector probe according to the invention.

FIGS. 1 & 1A show a detector probe 10, comprising a support incorporating a printed circuit board 12. A plurality of detectors 14 are mounted on the circuit board in a linear arrangement. A copper heat pipe 18, having water as its cooling fluid, is installed in close proximity to the detectors. A section through a detector probe is shown in FIG. 2. A circuit board 12, carrying Geiger-Müller (GM) tubes 14, is mounted on a support board 20, having a perpendicular portion to form a T-shaped cross-section. Power cables 24, carrying a high voltage supply to the GM tubes, and data cables 26 for carrying signals from the GM tubes to counting modules in a control housing, are run along the angle of the T-shaped support board. The detector probe is installed within a protective plastic tubular enclosure 30 which is then installed within a cylindrical dip pipe 34. Insulation 32 is provided between the tube 30 and the dip pipe.

DETAILED DESCRIPTION OF THE INVENTION

Figure 3:
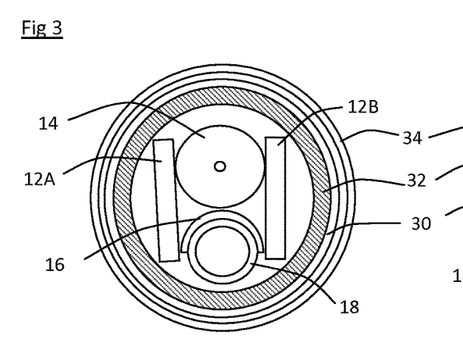
FIG. 3: A section through a second embodiment of a detector probe according to the invention.

A sectional view of an alternative embodiment of the invention is shown in FIG. 3. In this embodiment, GM tube 14 is supported on the heat pipe 18. Pad 16 is formed from Sil-Pad™ 1500ST thermally conductive elastomer to provide thermal contact between the GM tube and the heat pipe and also electrical insulation between them. Printed circuit boards 12A and 12B are mounted on either side of and electrically connected to the GM tube, and transport power, control signals and measurement signals between the GM tube and the power source, electrical control and signal processing apparatus housed within a separate housing. The high voltage supply circuit to power the GM tubes is carried on circuit board 12A, whilst the electrical components of the driving circuit are housed on board 12B. In this embodiment, insulation 32 is located between a protective plastic cover 30 and the components of the detector probe.

Figure 4:
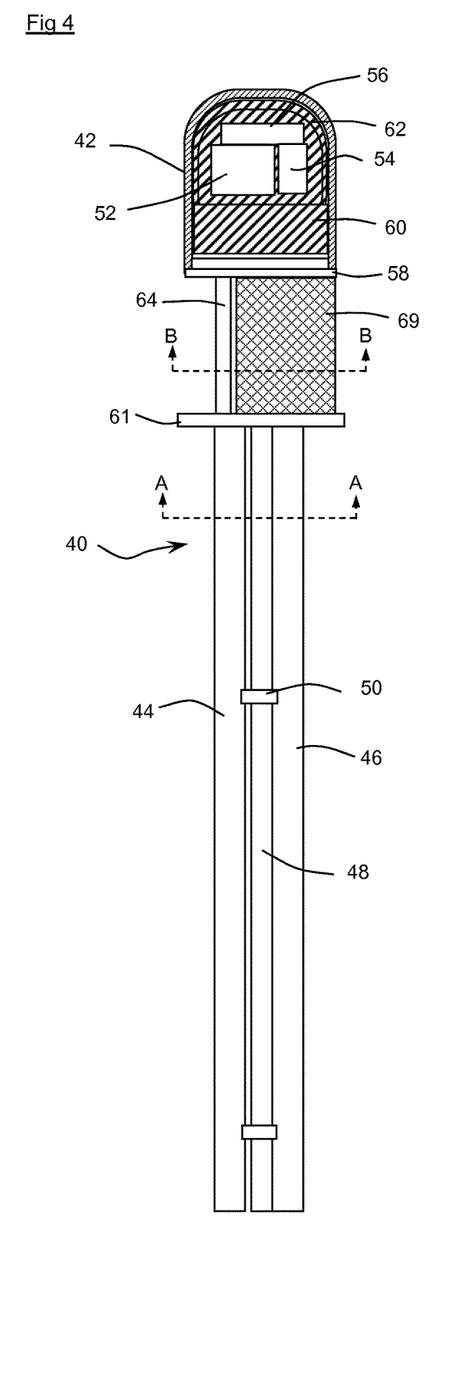
FIG. 4: A schematic diagram, partially in longitudinal section of a density profiler according to the invention.

FIG. 4 shows an elevation of a density profiler instrument 40 according to a preferred embodiment of the invention. The instrument comprises a steel housing, shown in section, comprising a support structure 58 and a domed cover 42. The housing contains at least a high voltage generator 52, data loggers, counters, signal processing means and data processors 54, means for supplying power to the voltage generator 56 and electrical equipment and means for transmitting information between the data processors and an external location. A layer of insulation 60 is packed between the electrical equipment contained in the housing and the support bracket 61 to which the dip tubes 44, 46 and 48 are mounted. Further insulation 62 is provided around the inside walls of the housing. A source array is housed in tube 44 and two detector probes are housed in tubes 46 and 48. The tubes are braced together for stability by braces 50. FIG. 4B shows a transverse section through the instrument along lines B-B. The domed cover 42 in which the electronic and power equipment are housed is located directly above the tubes 44, 46 and 48, supported on a flange 58 which bears onto metal shroud 69. A heat sink 66 is supported between the support structure 58 and the top of the source and detector arrays. The heat sink includes sockets 67 for receiving the upper ends of heat pipes which pass through the detector probes. The heat sink has fins 68 for assisting with the dissipation of heat from the heat sink. An expanded metal shroud 69 surrounds and protects the heat sink. Electrical connections, including power and data cables pass between the components in the housing and detector probes housed in tubes 46 and 48 through the conduit 64.

Figure 4A:
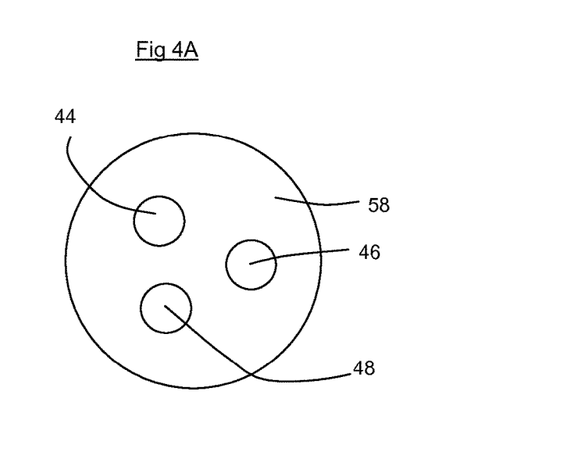
FIG. 4A: A schematic diagram of transverse section through line A-A of FIG. 4.
Figure 4B:
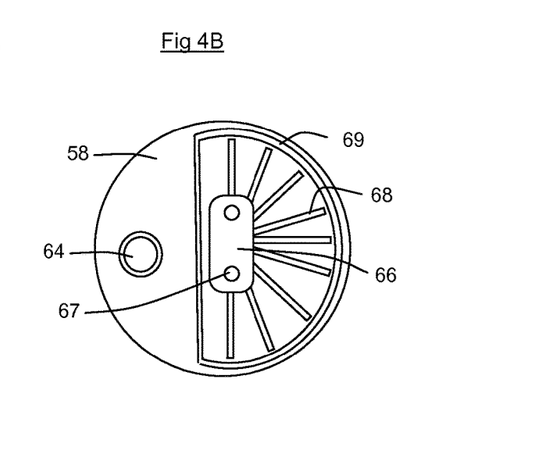
FIG. 4B: A schematic diagram of transverse section through line B-B of FIG. 4.

FIG. 4A shows a transverse section through the instrument along lines A-A and shows the configuration of the tubes 44, 46, 48 relative to each other and the housing 42.

Figures 5, 6:
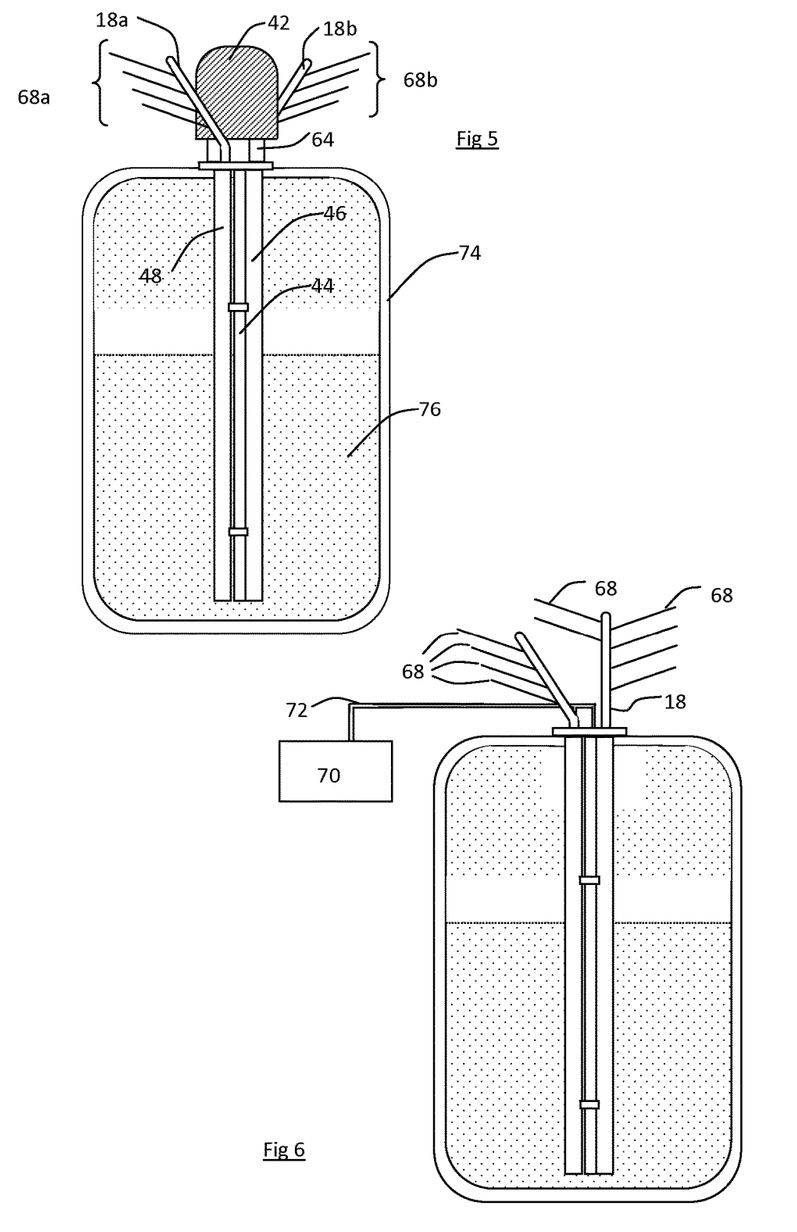
FIG. 5: A schematic section through a vessel in which one embodiment of a density profiler according to the invention is installed.
FIG. 6: A schematic section through a vessel in which a different embodiment of a density profiler according to the invention is installed.

FIG. 5 shows a vessel 74 containing a liquid 76. A density profiler passes through a flanged aperture in the vessel. The density profiler has two detector probes housed in tubes 46 and 48. Each detector probe comprises a heat pipe 18a, 18b which extends above the top of the tube in which the probe is housed. The domed cover 42 in which the electronic and power equipment are housed is located directly above the tubes 44, 46 and 48, supported on supports 64 through which power and data cables pass. The heat pipes are angled in the region of the supports 64 in order to accommodate the dome 42. The portion of the heat pipe external to the detector probe tube is provided with fins 68 in order to more rapidly dissipate heat from that portion of the heat pipe.

FIG. 6 depicts an alternative embodiment of a profiler in which the power source and electronic components are housed in a box 70 located away from the top end of the detector and source arrays. One or more cables 72 communicate between box 70 and the detector probes in order to carry power and electrical signals. The heat pipes 18 extend from the detector probes as before but need not be bent in this embodiment. The number and location of cooling fins 68 may be varied according to the requirements of the location. The heat pipes may or may not be angled in this embodiment.

The invention claimed is:

1. A nucleonic instrument for measuring a characteristic of one or more material phases within a container, comprising:
   at least one source of ionising radiation comprising alpha particles, beta particles, gamma radiation and/or neutrons;
   at least one detector probe configured for detecting said ionising radiation comprising a linear array of radiation detectors spaced apart along a heat pipe for cooling the detectors, the detectors being mounted in thermal contact with and physically supported on the heat pipe;
   a power source; and
   an electronic apparatus comprising a control unit and a signal and data processing means for calculating a characteristic of the material phases using signals generated by the detectors in response to radiation received from the radiation sources,
   wherein the nucleonic instrument is a level gauge or a density profiler.

2. The nucleonic instrument according to claim 1, wherein said instrument is a density profiler and further comprises a linear array of sources of ionising radiation.

3. The nucleonic instrument according to claim 1, wherein said source of ionising radiation is a source of gamma radiation.

4. The nucleonic instrument according to claim 1, wherein at least one of said heat pipes is provided with heat-dissipating means.

5. The nucleonic instrument according to claim 4, wherein said heat-dissipating means comprises a heat sink.

6. The nucleonic instrument according to claim 1, wherein said instrument is a level gauge and the source of ionising radiation is a source of gamma radiation.

7. The nucleonic instrument according to claim 1, wherein said instrument is a density profiler and the source of ionising radiation is a source of gamma radiation.

8. The nucleonic instrument according to claim 2 wherein said source of ionising radiation is a source of gamma radiation.

9. The nucleonic instrument according to claim 1, wherein said detector is selected from the group consisting of Geiger-Muller tubes and scintillation detectors.

10. The nucleonic instrument according to claim 1, wherein said heat pipe contains a liquid having a freezing point <−10° C.

11. The nucleonic instrument according to claim 1, comprising two or more heat pipes joined together using a thermally conductive coupling.

12. The nucleonic instrument according to claim 1, wherein at least one of said radiation detectors is mounted on said heat pipe and separated therefrom by means of a material which is thermally conductive and electrically insulating.

* * * * *